United States Patent [19]

Nelson

[11] Patent Number: 4,814,492

[45] Date of Patent: Mar. 21, 1989

[54] METHOD OF PREPARING ALKYL ACRYLATES

[75] Inventor: Edward C. Nelson, Lagrangeville, N.Y.

[73] Assignee: Texaco Inc., White Plains, N.Y.

[21] Appl. No.: 101,895

[22] Filed: Sep. 28, 1987

[51] Int. Cl.$^4$ .............................................. C07C 67/36
[52] U.S. Cl. ..................................... 560/207; 560/206
[58] Field of Search ................................ 560/207, 206

[56] References Cited

U.S. PATENT DOCUMENTS 3,397,225  8/1968  Fenton ................................ 560/207

Primary Examiner—Paul J. Killos
Attorney, Agent, or Firm—Robert A. Kulason; James J. O'Loughlin; Vincent A. Mallare

[57] ABSTRACT

A method for producing alkyl acrylates by reacting ethylene, CO, $O_2$ and an alkanol in the presence of a $PdCl_2/CuCl_2$ catalyst to produce an alkyl propionate which is passed over a base-treated zeolite catalyst to produce the alkyl acrylate.

19 Claims, No Drawings

METHOD OF PREPARING ALKYL ACRYLATES

BACKGROUND OF THE INVENTION

Field of the Invention

This invention relates to the preparation of alkyl acrylates. More particularly it relates to a continuous, catalytic process for the preparation of alkyl acrylates (AA).

In the process of upgrading and refining crude petroleum, an objective of the refiner is to separate chemical-grade feedstocks from fuel-grade feedstocks. Chemical grade feedstocks generally afford a higher return because the products derived from them are substantially more valuable to the ultimate consumer of the products. One such family of petroleum derived products is the acrylate group. Acrylates are presently made from propylene in a two-step process. By this process propylene is oxidized in the vapor phase over a heterogeneous Co-Fe-Bi-Mo catalyst to acrolein. The acrolein is subsequently oxidized to acrylic acid over a second heterogeneous catalyst which typically contains Mo, Va and W. The yield of acrylic acid is 80 percent in two steps. The lower alkyl acrylates (AA) are produced by esterification while the higher acrylates are produced by transesterication of the lower acrylates. Most of the acrylic acid produced is converted to either methyl or ethyl acrylate for eventual use in surface coatings, fibers and plastics. The overall process starts with the propylene and produces methyl or ethyl acrylate in three steps.

Thus, it is an object of the present invention to prepare methyl or ethyl acrylate from ethylene, carbon monoxide, oxygen and the appropriate alcohol in a two-step process by the oxidative carbonylation of ethylene and CO and methanol.

Disclosure Statement

U.S. Pat. No. 3,579,568 discloses a process for oxidatively carbonylating ethylene with PdCl2/CuCl2 catalyst at 80° C. and 925 psig. The reaction is catalytic in metal and uses oxygen as the oxidant. The product contains a mixture of methyl 3-methoxypropionate (44%) methyl acrylate (0.5%), acetaldehyde (21%), dimethyl ether (8%) and methyl propionate (10%).

U.S. Pat. No. 3,755,421 discloses a process for preparing ethyl acrylate from ethylene, CO, oxygen and ethanol in the presence of a PdCl2/benzoquinone catalyst. The process is carried out at 100° C. and 1000 psig total pressure but affords a product containing ethyl succinate as a by-product.

Honda, et al., Japanese Patent No. 15436/1972 (p. 47) discloses a process for preparing methyl acrylate by a disproportionation-esterification between acrylic acid and methyl 3-methoxypropionate. In the process, 1-2 moles of acrylic acid per mole of methyl 3-methoxypropionate is used to produce an 80 percent yield of methyl acrylate. The process is carried out at 100° C. over a sulfuric acid/cupric sulfate catalyst.

SUMMARY OF THE INVENTION

This invention is directed to a continuous method of preparing ($C_1$–$C_5$) alkyl acrylates. The method comprises:

(a) reacting ethylene with CO, $O_2$ and a ($C_1$–$C_5$) alkanol in the presence of a $PdCl_2/CuCl_2$ catalyst to form a ($C_1$–$C_5$) alkyl methoxy propionate;

(b) contacting the propionate with a catalyst treated with a hydroxide to produce a ($C_1$–$C_5$) alkyl acrylate product; and (c) recovering the ($C_1$–$C_5$) alkyl acrylate product.

According to the present invention, alkyl acrylates such as methyl and ethyl acrylates are preferably made for use particularly in fibers and plastics.

DRAWING

The present method will be more clearly understood from a review of FIG. 1 which is a flow diagram of the present process showing the reaction steps used to prepare alkyl acrylates.

As illustrated in FIG. 1, a process is provided for the conversion of ethylene, carbon monoxide, methanol and oxygen to methyl acrylate by a two-step process. The first step consists of the oxidative carbonylation of ethylene to afford methyl 3-methoxypropionate in a substantially pure form by a liquid phase, low pressure process. The second step consists of a base-catalyzed, vapor phase conversion of methyl 3-methoxypropionate (MMP) to methyl acrylate and methanol. The present process and its advantages are more clear when considering the drawing (FIG. 1) in conjunction with the following description of the present invention.

DESCRIPTION OF THE INVENTION

In preparing alkyl acrylates (AA) according to the present invention, a novel two-step process is employed. An alkyl acrylate (AA) such as methyl acrylate (MA) is prepared by the oxidative carbonylation of ethylene with CO and methanol in the presence of a catalyst. This process may proceed catalytically to afford methyl 3-methoxy propionate in either two steps (eq. 1 and 2 below) or one step (eq. 3). The present invention relates specifically to a one-step process but the advantages contained therein might be readily applied to a one-step process as illustrated in the equations below:

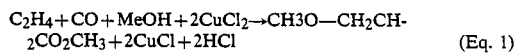

$$C_2H_4 + CO + MeOH + 2CuCl_2 \rightarrow CH_3O\text{—}CH_2CH_2CO_2CH_3 + 2CuCl + 2HCl \quad \text{(Eq. 1)}$$

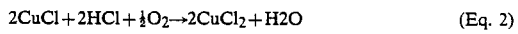

$$2CuCl + 2HCl + \tfrac{1}{2}O_2 \rightarrow 2CuCl_2 + H_2O \quad \text{(Eq. 2)}$$

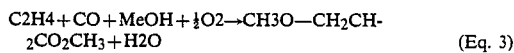

$$C_2H_4 + CO + MeOH + \tfrac{1}{2}O_2 \rightarrow CH_3O\text{—}CH_2CH_2CO_2CH_3 + H_2O \quad \text{(Eq. 3)}$$

In the presence of a palladium chloride catalyst, the reaction in Eq. 1 proceeds readily at less than 100 psig and 100° C. Under these conditions the reaction proceeds with a productivity of about 0.132 grams MMP/cc -hr and with an 89 percent selectivity to methyl 3-methoxypropionate (MMP). The major side-product detected is dimethyl ether at a 5-6 percent selectivity. Several advantages of the present process, exist over the known processes and those disclosed in the above disclosure statement, including:

(a) The present process produces almost exclusively methyl 3-methoxypropionate (MMP) with very high selectivity. The major side-product, dimethyl ether, is an easily separated low-boiling liquid; and (b) The present process proceeds readily even at low pressure. Because of the corrosive nature of the catalyst systems (chloride containing) expensive metallurgy is required for construction of high-pressure reactors. In contrast, this process proceeds at low pressure so that glass-lined or teflon-lined carbon steel reactors could be employed.

Reoxidation of the CuCl to CuCl$_2$ could be carried out in a subsequent step (Eq. 2) or the process might be run in one step (Eq. 3) using oxygen as the ultimate oxidant.

The second step of the process consists of a base catalyzed elimination of methanol from MMP to produce methyl acrylate (MA). The process may be demonstrated by passing a mixed stream of MMP and nitrogen over a KOH-treated zeolite at 380° C. in a fixed-bed, downflow reactor. Under these conditions, the conversion of MMP can be 55 percent and the selectivity to methyl acrylate can be 100 percent.

In the present method the (C$_1$–C$_5$) alkanols that may be used include methanol, ethanol, propanol, butanol, pentanol and the like. The (C$_1$–C$_5$) alkanol is reacted with ethylene, CO and O$_2$ in the presence of a PdCl$_2$/CuCl$_2$ catalyst to form a corresponding (C$_1$–C$_5$) alkyl methoxy propionate. The reaction mixture may include an inert cosolvent which can be a cosolvent selected from the group consisting of xylene, toluene, benzene, dimethylformamide (DMF), dimethylsulfoxide (DMSO) and N-methylpyrolidone (NMP).

The methoxy propionate is contacted with a base-treated catalyst which is preferably a zeolite catalyst or some suitable equivalent thereof, in the presence of a polymerization inhibitor such as p-methoxy phenol or hydroquinone. The inhibitor is generally present at a concentration of about 25 ppm to 2500 ppm. The zeolite catalyst consists of a support material selected from the group consisting of zeolite, silica, alumina and titania.

The base material used to treat the catalyst is selected from the group consisting of an alkali metal, or alkaline earth metal, hydroxide, carbonate or bicarbonate.

The alkali metal hydroxide may be KOH, NaOH, CsOH or LiOH with KOH being preferred. The alkaline earth metal hydroxide may be Ca(OH)$_2$, Ba(OH)$_2$ or Mg(OH)$_2$. Similarly, the alkaline earth metal (or alkali metal) carbonate (or bicarbonate) may be CaCO$_3$, MgCO$_3$, BaCO$_3$, NaHCO$_3$, Li$_2$CO$_3$, KHCO$_3$, LiHCO$_3$, Na$_2$CO$_3$K$_2$CO$_3$.

In the present method, the proportions of the different material used may be important. Thus, the ratio of CO to ethylene is from about 1:10 to about 10:1, whereas the ratio of O$_2$ to CO and ethylene is from about 1:50 to about 1:3. As for the catalyst used in the first step of the present process, the ratio of PdCl$_2$ to CuCl$_2$ is from about 1:1000 to about 1:10.

In the overall method of the present invention, the first step where the propionate is formed is carried out continuously at a temperature of about 15° C. to about 100° C. and under a pressure of about 1 to about 10 atmospheres. In contrast, the second step of the method where the acrylate product is produced is continuously carried out at a temperature ranging from about 75° C. to about 500° C. and under a pressure of from about 10 psig to about 200 psig.

The advantages of the present process and invention, which are selectivity and productivity, will bemore clearly appreciated in the following examples.

EXAMPLE I

Palladium chloride 0.226 g), cupric chloride (3.36 g) and anhydrous methanol (25 mL) were added to a pressure bottle containing a magnetic stirrer. The bottle was attached to a gas manifold and the mixture was pressurized to 75 psig with argon and vented three times. The pressure bottle was warmed in a hot oil bath to about 60°–65° C. for 10 minutes with stirring. The bottle was pressurized to 75 psig with a 50/50 (vol. %) mixture of ethylene and CO, held at this temperature for 10 minutes and then cooled and vented. The bottle was rapidly cooled in an ice-bath, filtered and made up to 25 mL with methanol. The mixture was analyzed by GLC on a ⅛"×2M ss 10% OV-101 column. The calculated productivity was 0.132 g MMP/cc-hr and the selectivity to MMP. was 89 percent. Dimethyl ether was the only other side product obtained in 5 percent selectivity.

EXAMPLE II

Ten g of zeolite (3 Å molecular sieves) were crushed and sieved to 40–60 mesh, dried under vacuum at 225° C. overnight and cooled to room temperature in a desicator. Three g of the support was treated with a 10 wt. % solution of KOH in water to the incipient wetness point. The catalyst was dried at 225° C. overnight under vacuum and cooled in a desiccator to form a catalyst with a loading of 0.036 g KOH/g zeolite.

EXAMPLE III

A ½" stainless steel tube was loaded with 3 grams of the catalyst prepared in Example 2. The tube was heated to 380° C. under a stream of nitrogen at a pressure of 20 psig and flow rate of 20 cc/min. A solution of p-methoxyphenol (50 mg) in MMP (11.0 g) was added to the top of the catalyst bed at a rate of 0.20 cc/min. The product (9.5 g) was collected at the bottom of the reactor in a dry-ice acetone trap and analyzed by GLC on an ⅛"×2 m ss 15% FFAP column. The product consisted of a mixture of unconverted MMP (4.9) and methyl acrylate (4.6 g). Methanol was absorbed into the catalyst bed. Methyl acrylate productivity was 1.5 g MA/g catalyst-hr with a selectivity of nearly 100 percent based on unconverted but recovered MMP.

I claim:

1. A continuous method of preparing an alkyl acrylate comprising:
    (a) reacting ethylene CO, O$_2$ and a (C$_1$–C$_5$) alkanol in the presence of a PdCl$_2$/CuCl$_2$ catalyst to form a (C$_1$–C$_5$) alkyl methoxy propionate;
    (b) contacting said propionate with a base-treated catalyst to produce a (C$_1$–C$_5$) alkyl acrylate product; and
    (c) recovering said (C$_1$–C$_5$) alkyl acrylate product.

2. A continuous method of preparing methyl acrylate comprising:
    (a) reacting ethylene with CO, O$_2$ and methanol in the presence of a PdCl$_2$/CuCl$_2$ catalyst to form methyl-3-methoxy-propionate;
    (b) contacting said propionate with a base-treated catalyst treated with KOH to produce methyl acrylate; and
    (c) recovering the methyl acrylate product.

3. A continuous method of preparing an ethyl acrylate comprising:
    (a) reacting ethylene with CO, O$_2$ and ethanol in the presence of a PdCl$_2$/CuCl$_2$ catalyst to form ethyl-3-methoxy-propionate;
    (b) contacting said propionate with a base-treated catalyst to produce ethyl acrylate; and
    (c) recovering the ethyl acrylate product.

4. The method of claims 1, 2 and 3, wherein said catalyst is a base-treated zeolite catalyst.

5. The method of claims 1, 2 and 3, wherein said base material used to treat the catalyst is selected from the group consisting of an alkali metal or alkaline earth metal hydroxide, carbonate or bicarbonate.

6. The method of claim 5, wherein said alkali metal hydroxide is selected from the group consisting of KOH, NaOH, LiOH and CsOH.

7. The method of claim 5, wherein said alkaline earth metal hydroxide is selected from the group consisting of $Ca(OH)_2$, $Ba(OH)_2$ and $Mg(OH)_2$.

8. The method of claim 5, wherein said alkaline earth metal (or alkali metal) carbonate (or bicarbonate) is selected from the group consisting of $CaCO_3$, $MgCO_3$, $BaCO_3$, $NaHCO_3$, $Li_2CO_3$, $KHCO_3$, $LiHCO_3$, $Na_2CO_3$ or $K_2CO_3$.

9. The method of claims 1, 2 and 3, wherein said methoxypropionate is contacted by a base-treated zeolite catalyst in the presence of a polymerization inhibitor selected from the group consisting of p-methoxyphenol and hydroquinone.

10. The method of claim 1, wherein step (a) of the method is carried out continuously at a temperature of about 25° C. to about 100° C. and under a pressure of about 1 to about 10 atmospheres.

11. The method of claim 1, wherein the ratio of CO to ethylene is from about 1:10 to about 10:1.

12. The method of claim 1, wherein the ratio of $O_2$ to CO and ethylene is from about 1:50 to about 1:3.

13. The method of claim 1, wherein the ratio of palladium chloride ($PdCl_2$) to cupric chloride ($CuCl_2$) is from about 1:1000 to about 1:10.

14. The method of claim 1, wherein the reaction mixture is predominantly a ($C_1$–$C_5$) alkanol or a mixture of a ($C_1$–$C_5$) alkanol and an inert cosolvent.

15. The method of claim 14, wherein said cosolvent is selected from the group consisting of xylene, toluene, benzene, dimethylformamide, dimethylsulfoxide (DMSO) and N-methylpyrolidone (NMP).

16. The method of claim 5, wherein said base-treated zeolite catalyst consists of a support material selected from the group consisting of a zeolite, silica, alumina and titania.

17. The method of claim 9, wherein the polymerization inhibitor is present in the feed or catalyst at a concentration of about 25 ppm to about 2500 ppm.

18. The method of claim 1, wherein said catalyst temperature of step (b) ranges from about 75° C. to about 500° C.

19. The method of claim 18, wherein the total pressure is from about 10 psig to about 200 psig.

* * * * *